United States Patent
Zambotto et al.

(10) Patent No.: US 7,709,530 B2
(45) Date of Patent: May 4, 2010

(54) RODENTICIDAL COMPOSITION IN THE FORM OF VEGETABLE PASTE

(75) Inventors: Pierpaolo Zambotto, Cartura Padova (IT); Massimo Tagliaro, Albignasego Padova (IT)

(73) Assignee: Zapi Industrie Chimiche S.p.A., Conselve-Padova (IT)

( * ) Notice: Subject to any disclaimer, the term of this patent is extended or adjusted under 35 U.S.C. 154(b) by 1241 days.

(21) Appl. No.: 10/552,235

(22) PCT Filed: Mar. 26, 2004

(86) PCT No.: PCT/EP2004/003310

§ 371 (c)(1),
(2), (4) Date: Oct. 6, 2005

(87) PCT Pub. No.: WO2004/098286

PCT Pub. Date: Nov. 18, 2004

(65) Prior Publication Data

US 2006/0222676 A1    Oct. 5, 2006

(30) Foreign Application Priority Data

May 7, 2003  (IT)  .......................... MI2003A0919

(51) Int. Cl.
*A61K 31/198* (2006.01)
*A61K 31/137* (2006.01)
(52) U.S. Cl. ...................................... 514/567; 514/649
(58) Field of Classification Search ........................ None
See application file for complete search history.

(56) References Cited

U.S. PATENT DOCUMENTS

| 1,858,177 | A | * | 5/1932 | Aeschlimann | 514/490 |
| 5,002,768 | A | * | 3/1991 | Kondo et al. | 424/408 |
| 5,720,951 | A | * | 2/1998 | Baker | 424/84 |
| 6,136,340 | A |   | 10/2000 | Chuhran | |
| 2005/0181003 | A1 | * | 8/2005 | Endepols et al. | 424/410 |

FOREIGN PATENT DOCUMENTS

| GB | 2081583 | | 2/1982 |
| JP | 02149501 | A * | 6/1990 |
| WO | WO 03/094612 | | 11/2003 |

OTHER PUBLICATIONS

P.A. Anadu: "A study of bait selection in small African rodents" ACTA Theriologica vol. 24, No. 36, 1979, pp. 501-511.
C. Sivaprakasam, et al.: "Laboratory evaluation of bait base for the control of Indian field mouse, mus booduga (Gray)" Indian Journal of Experimental Biology, vol. 33, Jul. 1995, pp. 497-499.
M.S. Ahamad: Laboratory evaluation of some vegetable oils as bait enhancers against roof rat, Rattus rattus Pakistan Journal of Zoology vol. 26, No. 2, 1994, pp. 93-97.

* cited by examiner

*Primary Examiner*—David J Blanchard
*Assistant Examiner*—Kyle Purdy
(74) *Attorney, Agent, or Firm*—Hedman & Costigan, P.C.; James V. Costigan

(57) ABSTRACT

The present invention relates to a rodenticidal composition in the form of fresh paste for enticing mice and rats wherein the flour used is mainly of a vegetable origin and the fatty matter incorporated essentially consists of palm oil.

2 Claims, No Drawings

RODENTICIDAL COMPOSITION IN THE FORM OF VEGETABLE PASTE

The present invention relates to a rodenticidal composition in the form of vegetable paste.

In particular, the present invention relates to a preparation for enticing mice, rats, moles and voles, in the form of fresh bait having a reduced content of substances of animal origin.

The present invention originates in the field of chemical systems for preventing and treating infestations on the part of murine species.

It is well known that systems for fighting mice and rats have rapidly evolved due to the increase in the murine population and progress of urban infestations in recent years.

The control of infesting murine populations has become increasingly more important as rats and mice have a parasitic life which causes an impoverishment of available food resources, not only due to the amount of food they consume, but also as a result of the huge amounts which pollute.

As is known, the common disinfestation systems normally used, adopt mechanical, electronic and chemical means. The latter essentially consist of preparations for oral consumption which, once eaten by the animal, interfere with its vital processes, causing its death.

The most commonly used chemical means consist of rat poison baits, rodenticide preparations with an enticing ingesting effect.

These preparations contain a poisoning substance, normally consisting of one or more anticoagulant active principles which poison a bait. The greater the enticing effect and attractiveness of the bait, the higher the probability will be that the active principle has been taken in a amount which is lethal for the animal.

The rat poisoning preparations which are currently on the market, have different forms, for example pellets, covered with paraffinated products, powders, gels, cereal blends, or in the form of a paste, also called fresh bait.

Among the different types of baits present on the market, the paste form has proved to be the most desirable formulation. These paste baits are based on flours amalgamated with a fatty matter, consisting of animal or vegetable fat products to which antioxidant products are added in order to prevent them from becoming rancid.

Although the presence of the fat phase is essential for conferring a high palatability to the preparation, it has the drawback of making the fats transude excessively in liquid form, when the bait is exposed to high temperatures, for example during the summer or inside poisoning stations.

It has also been observed that the fat phase normally used is responsible for chemical instability: rancidity and oxidation are typically phenomena observed. Rancidity diminishes the palatability of the bait, and consequently mice and/or rats consume it in a lower amount, whereas oxidation causes a considerable decrease in the titer of the active principles, and consequently the mice and/or rats must eat more bait in order to have lethal effects, thus increasing the possibility of the development of resistance phenomena to the action of the anticoagulants.

It is therefore desirable to have baits in paste form with a high stability also in a hot-humid climate, and stable to phenomena caused by the chemical degeneration of the fat phase.

Although the rodenticidal preparations in paste form which are currently available on the market, have a reasonable enticement capacity with respect to various murine species, they have high quantities of substances of animal origin in their formulations.

In particular, vegetable flour is used in combination with lard, a prevalently saturated fatty substance with reduced amounts of linoleic acid. This animal fat is widely used as it is obtained at a low cost from melting the inner fat of a perineal, mesenteric or abdominal origin of pigs, with subsequent discoloring, clarification and filtration.

Tallow, which is a fatty substance obtained by melting the adipose tissues of bovines, can also be used.

It has been observed however that bait formulations in paste form based on animal fats, such as lard or tallow or particular fats of a vegetable origin, tend to excessively transude when packed in bags or packets ready for use.

The necessity is therefore felt for having fat phases alternative to lard, without jeopardizing the palatability, which is necessary for enticing the various murine species.

The addition to lard of vegetable oils such as peanut oil, corn oil, sunflower oil, have not as yet provided encouraging results, as the above rancidity and oxidation phenomena can occur, with the result that mice and rats do not appear to be particularly tempted by the degeneration phenomena of the fatty phase.

It is also well known that recent regulations relating to zootechnics are imposing various restrictions in the use of different substances of animal origin specifically in the feeding of breeding animals.

These restrictions derive from the appearance and recent diffusion of some illnesses of an obscure origin, such as BSE or scrapies. The origin of these illnesses does in fact seem to be attributable to the use of flour or other derivatives of animal origin in animal farming.

In particular, one of the most probable explanations for the mad-cow epidemic explosion is that the animals struck by the disease were fed with fodder containing flour and proteins of an ovine origin coming from meat and bone powder.

The necessity is therefore strongly felt for limiting the use of flour or food of animal origin which can contain or carry prion, the infesting protein which is believed to be the origin of degenerative neurological illnesses in cattle, of scrapies in sheep and of Creutzfeld-Jacob's disease in human beings.

The problem of substituting flour and animal components in rat-poisoning baits is not easy to solve, as it has been observed that various ingredients of animal origin are particularly palatable to rodents and thus constitute an alluring component which is difficult to substitute with substances of vegetable origin.

The necessity is consequently felt for having new preparations with a rat-poisoning action in fresh paste which preserve their palatability with respect to the most varied murine species, and do not contain food products potentially harmful for other animals and human beings, as the latter, especially during the productive phase of rat-poisoning baits, can come into contact with components of an animal origin.

One of the main objectives of the present invention is to provide a rat-poisoning composition for the enticement of mice and rats in the form of a fresh bait of a vegetable origin and consequently with minimum risks of transmitting the infectious agent responsible for degenerative neurological diseases to other animals.

Another aspect of the present invention consists of providing a rat-poisoning preparation in the form of a fresh bait, mainly of vegetable origin, which has a high palatability with respect to various murine species.

A further objective consists of providing a rat-poisoning preparation in the form of fresh bait, mainly of vegetable origin, which is stable and not subject to rancidity and oxidation, thus maintaining the titer of active principle and a high palatability of the bait.

In view of these and other objectives which will appear more evident hereafter, a rodenticidal composition in the form of vegetable paste is provided, in accordance with a first aspect of the present invention, comprising:

a fraction based on carbohydrates, prevalently of a vegetable origin;

a fraction based on a fatty matter, prevalently of a vegetable origin;

at least one rodenticidal active principle, characterized in that said fraction of fatty matter comprises a vegetable oil having an iodine index lower than or equal to 70, preferably lower than 60, even more preferably ranging from 48 to 53.

According to a particularly preferred embodiment of the invention, said vegetable oil is palm oil, suitably of the refined type.

Coconut oil and its blends with palm oil is also included among vegetable oils having an iodine number lower than 70, which can be used within the scope of the invention.

Within the scope of the present invention, the term fraction based on carbohydrates prevalently of a vegetable origin, means that the carbohydrate component of a vegetable origin is equal to or higher than 80% by weight, more preferably higher than 90% and even more preferably higher than 95% by weight with respect to the total quantity of carbohydrates present in the rodenticidal mixture. Similarly, the term fraction of fatty matter prevalently of a vegetable origin, has the corresponding meaning.

According to an embodiment of the invention, the fraction based on carbohydrates incorporated in the composition of said mixture, is completely of a vegetable origin.

According to another embodiment of the invention, the fraction based on fatty matter of the mixture exclusively comprises one or more oils of a vegetable origin, advantageously palm oil.

The fraction based on carbohydrates conveniently comprises flour and sugar of a vegetable origin.

It has been found that the risk of transmitting neurological diseases to infesting murine species and to other animals which can come into contact with the same, can be considerably reduced by using selected components for rodenticidal baits in the form of fresh paste.

In particular, the presence of quantities lower than 20%, preferably lower than 10% and, even more preferably, lower than 5% by weight of polysaccharides and/or fatty matter of an animal origin, increases the sanitary safety for the use of the rat-poisoning preparation and, in particular, the complete substitution of the fat fraction of animal origin with a fraction of vegetable origin with an iodine number lower than 70, also allows the stability of the composition itself to be increased, with a reduction in the occurrence of transuding of the fat phase and the rancidity and oxidation phenomena mentioned above.

It has been specifically found that the substitution in rat-poisoning preparations in paste form, of the animal fat component with a vegetable oil having an iodine number selected between 48 and 53, typical of palm oil, not only reduces the risks of transmitting infections of degenerative neurological illnesses, but also increases the stability of the composition. Palm oil is in fact a particularly stable vegetable oil and, as such, is poorly subject to rancidity and oxidation phenomena.

The Iodine Number represents the grams of iodine that can be fixed by 100 g of fatty substance.

This index represents the total unsaturation degree of higher fatty acids, both free and combined.

A method for its determination is based on the addition reaction that the double bonds can undergo in the presence of halogens. Chlorine iodide, a polar molecule produced by the reaction between iodine trichloride and molecular iodine, is used in order to increase the reactivity of the double bonds, as a substitute of the halogen molecular species, which contain pure covalent bonds. This reaction is the demonstration of the Wijs reagent.

The possible iodine number values which can be observed, depend on the nature of the triglyceride under examination.

For example, solid fats, having high percentages of saturated glycerols, have a low iodine number, normally lower than 50. Non-siccative oils, such as olive oils, have values which can be higher than 90. Siccative oils, such as linseed oil or fish oil, have values even higher than 120. This is plausible considering the high unsaturation degree present in the aliphatic chains of the fatty acids present in these products.

A low iodine number, possibly lower than 70, means a low number of double bonds in the oil molecules, consequently a higher stability of the molecule to oxidation and therefore to rancidity or to the formation of aldehydes or secondary degradation compounds of both the fatty substances and the active principle contained in the bait.

Examples of the iodine number of vegetable oils for food and of the method for its calculation are provided in Example 6.

According to an embodiment, said fraction based on fatty matter is incorporated in the rodenticidal mixture of the invention, in an amount ranging from 15 to 35%, preferably between 20 and 30% by weight.

It has been unexpectedly found that the use of palm oil in rodenticidal baits considerably increases the palatability of the bait itself. Palm oil does in fact have organoleptic characteristics particularly appreciated by various murine species, such as mice and rats, with different food habits, which normally infest both urban and agricultural areas.

The palm oil which can be used within the scope of the invention, which is typically found in palm fruit, is obtained both from palms and from almonds or pits, which contain the seed. In particular, palm nut oil is obtained from the seeds, which, after shelling and grinding, are subjected to pressing under heat. The content of oil which can be typically obtained from the seed is equal to 43-51% of the seed weight.

The best quality oil, commercially known as palm nut oil, is obtained from the seeds, which, after shelling and grinding, are subjected to pressing under heat; it is rarely extracted by means of chemical solvents. The oil content ranges from 43 to 51% of the seed weight. From a chemical and organoleptic point of view, this oil is very similar to coconut oil, but has a higher content of oleic acid; it has a solid and butter-like consistency below 20° C., it has a white-yellowish colour, a pleasant taste and smells like coconut.

Palm nut oil has a varying degree of acidity, normally not higher than 15% and is mainly used for food purposes such as margarine or vegetable butter, or as partially hydrogenated oil; it is suitably refined and discolored for the above purposes.

An oil with a higher degree of acidity and therefore of a lower quality, is obtained from the fibrous pulp of palm fruits, by pressing under heat.

This oil, whose content ranges from 40 to 70% for each fruit, is mainly used for preparing soaps and cosmetics or, on an industrial level, as a lubricant.

The fraction based on carbohydrates in the rodenticidal composition in the form of vegetable paste according to the invention, advantageously has a content of flour of a non-vegetable origin reduced to 20% by weight, preferably lower than 10%, more preferably lower than 5% by weight with respect to the total weight of the composition itself.

According to an embodiment of the invention, the fraction based on carbohydrates is completely vegetable and there is therefore no flour of animal origin.

Suitable polysaccharide fractions include vegetable flours in general, such as flour from cereals, for example corn, rice, barley, oats, wheat and mixtures thereof, and glucose, saccharose, dextrose, inverted sugar, fructose, and other di- or polysaccharides alone or mixed.

The rodenticidal composition in the form of vegetable paste of the invention, suitably comprises a proteinic fraction also of a vegetable origin.

The rodenticidal composition of the invention has demonstrated a particularly appreciable behavior when subjected to palatability, stability and routine efficacy tests in the field.

The high stability of the composition is mainly due to the higher stability of the fatty phase used, essentially consisting of vegetable oil with a reduced iodine number, with particular reference to palm oil. The use of these oils, moreover, also allows the stability of the incorporated rodenticidal principle to be improved.

The greater palatability of the preparation of the invention can also be attributed to the considerable reduction in fatty matter subject to rancidity and to degradation, as a consequence of the use of selected vegetable oils which are subject to a very low oxidation process.

The use of selected vegetable oils also allows a decrease in degradation processes of the bait prepared, even when the environmental characteristics have a high degree of humidity and a high temperature. These characteristics allow the composition according to the invention to be prepared in all the various types of preparations present on the market.

According to another aspect of the present invention, a method is provided for the preparation of the composition according to the invention, which comprises mixing the flour with vegetable oil having an iodine number equal to or lower than 70, and with a rodenticidal active principle plus suitable additives and preservatives, so as to obtain a paste wherein the components are homogeneously mixed.

The active principles having a rodenticidal activity which can be typically incorporated in the paste, can be divided into two categories:

Acute or single-dose rodenticidal products;

Chronic or multi-dose rodenticidal products.

Natural and synthetic poisons belong to the first category: natural poisons include scilliroside and strychnine, whereas synthetic poisons include crimidine, sodium fluoro acetate and fluoro acetamide, zinc phosphide, norbormide, thallium sulphate, antu and alphachloralosium.

Even if the acute rodenticidal products are not as efficacious as the chronic ones (anticoagulants), they can be validly used in emergency situations, when the destruction of the murine population must be obtained in the shortest possible time.

The most suitable active principles for use in accordance with the present invention, are anticoagulants, typically present in the formulation in quantities ranging from 0.1 to 0.0001% by weight, preferably equal to about 0.005%.

The use of these molecules is preferable for two reasons: for their action procedure, not before 2-3 days after ingestion, regardless of the amount of food eaten, and for their relative safety, due to the fact that the amount of bait necessary for providing toxic effects is such as to make lethal intoxication of human beings, children and domestic animals improbable.

The types of anticoagulant products used can be divided according to their action procedure: multi-dose, or first generation anticoagulants and single-dose or second generation anticoagulants. Warfarin, coumachloro, coumatetralyl, coumafuril, pivaldione, difacinone and chlorofacinone are included in the first type; bromadiolone, difenacoum, brodifacoum, difethalone and flocoumafen and mixtures thereof, are included in the second type.

As an example, Bromadiolone is described below, having the following structural formula:

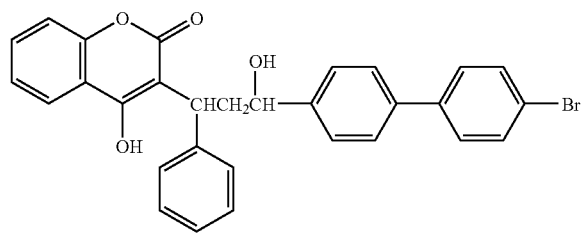

Active principles having an anticoagulant action can be advantageously used in the composition of the invention, in a percentage usually ranging from 0.001 to 0.1% in free or micro-encapsulated phase.

Bittering substances can be included in the composition of the present invention, for example Denatonium Benzoate and possibly substances which discourage accidental ingestion on the part of non-target species, such as dogs, cats, children.

The composition of the invention, in the form of fresh bait, should be placed in small amounts where there are rodents, care being taken to renew the bait before being completely consumed, in amounts of 10-20 g (1-3 mono-dose sachets) per square meter of surface to be protected.

It is preferable to avoid touching the product with bare hands, due to the diffident nature of rodents towards human odors, using rubber or PVC gloves. The fresh bait can be used for domestic, civil and industrial use, and is suitable for rat extermination to a limited or large extent, according to the amount used.

The following examples are provided for illustrative purposes only of the present invention and should in no way be considered as limiting the protection scope of the invention, as specified in the enclosed claims.

EXAMPLE 1

Formulation of a rodenticidal composition as a fresh vegetable paste according to the invention:

| | |
|---|---|
| superfine "00" flour | 49.1565% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| rat poisoning active principle | 0.005% |
| denatonium benzoate * | 0.001% |

EXAMPLE 2

Formulation of a rodenticidal composition as a fresh vegetable paste according to the invention:

|  |  |
|---|---|
| superfine "00" flour | 49.154% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| brodifacoum | 0.0075% |
| denatonium benzoate * | 0.001% |

EXAMPLE 3

Formulation of a rodenticidal composition as a fresh vegetable paste according to the invention:

|  |  |
|---|---|
| superfine "00" flour | 49.1605% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| flocoumafen | 0.001% |
| denatonium benzoate * | 0.001% |

EXAMPLE 4

Formulation of a rodenticidal composition as a fresh vegetable paste according to the invention:

|  |  |
|---|---|
| superfine "00" flour | 39.154% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| brodifacoum | 0.0075% |
| denatonium benzoate * | 0.001% |
| decorticated whole oats | 5.00% |
| wheat, barley, insufflated oats | 5.00% |

EXAMPLE 5

Formulation of a rodenticidal composition as a fresh vegetable paste according to the invention:

|  |  |
|---|---|
| superfine "00" flour | 39.154% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| brodifacoum | 0.0075% |
| denatonium benzoate * | 0.001% |
| granular dry apple | 5.00% |
| decorticated whole oats | 5.00% |
| wheat/rice, insufflated oats | 5.00% |

EXAMPLE 6

The iodine number values (**) of the main vegetable oils are indicated in the following table

TABLE 1

| Oil type | Iodine number |
|---|---|
| Peanut | 86-100 (92-95) |
| Rape | 94-106 (100) |
| Soybean | 120-140 (127-135) |
| Sesame | 102-116 (108) |
| Sunflower | 120-137 (133) |
| Corn | 108-128 (120) |
| Safflower | 135-150 (140) |
| Cotton | 101-117 (108) |
| Grape-stones | 126-142 — |
| Tea | 80-90 — |
| Olive | 79-88 (81-83) |
| Palm oil | 48-53 — |

(*) At 25° C.
(**) The data in brackets indicate the limits or the most common average values.

The above table shows that refined palm oil has the lowest iodine number (48-53) among all oils and vegetable fatty substances on the market, and consequently a very high stability to rancidity and oxidation.

1. Determination of the Iodine Number

The following method defines the determination of the iodine number in fats and oils, of animal and vegetable origin, hereinafter referred to as "fatty matter"

2. Definition

The following definition is used for the purposes of the present method:

2.1. Iodine number: the iodine mass absorbed by the sample under the conditions specified in the current international regulation. The iodine number is expressed as grams of iodine per 100 g of sample.

3. Principle

Dissolution of the substance to be analyzed in the solvent and addition of the Wijs reagent. After a certain period of time, addition of a solution of potassium iodide and water, and titration of the iodine released with a solution of sodium thiosulfate.

4. Reaction

The Wijs reagent, which is added in excess, quantitatively reacts with the double bonds existing in the aliphatic chains of the triglyceride:

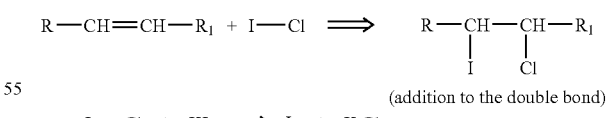

(addition to the double bond)

$$I\text{—}Cl + KI \Longrightarrow I_2 + KCl$$

(the excess of reagent releases iodine in the presence of KI).

The molecular iodine is then subjected to titration with thiosulfate. Starch-water as indicator.

5. Reagents

All of these must have an analytical grade.

5.1. Potassium iodide, solution of 100 g/l, not containing iodide or free iodine.

5.2. Starch, solution.

Pour 5 g of soluble starch into 30 ml of water, add this mixture to 1000 ml of boiling water, let it boil for 3 minutes and leave it to cool down.

5.3 Sodium thiosulfate, standard volumetric solution $(Na_2S_2O_3 \cdot 5H_2O)=0.1$ mole/l, standardized not more than 7 days before use.

5.4 Solvent, prepared by mixing equal volumes of cyclohexane and acetic acid.

5.5 Wijs reagent, containing iodine monochloride in acetic acid. It is convenient to use the Wijs reagent available on the market.

(The reagent contains 9 g of $ICl_3$+9 g of I in acetic acid).

6. Equipment

The usual laboratory equipment, in particular:

6.1 Glass weight-thimbles, suitable for the solution to be analyzed and for insertion into Erlenmeyer flasks (6.2).

6.2 Erlenmeyer flasks, having a capacity of 500 ml, with ground-glass stoppers and completely dry.

7. Preparation of the Sample of Substance to be Analyzed

The homogenized sample is dried on sodium sulfate and filtered.

8. Procedure 8.1 Substance to be Analyzed

The weight of the substance to be analyzed varies according to the expected iodine number, as indicated in the following table 2

TABLE 2

| Expected iodine number | Mass (g) of the substance to be analyzed |
| --- | --- |
| lower than 5 | 3.00 |
| from 5 to 20 | 1.00 |
| from 21 to 50 | 0.40 |
| from 51 to 100 | 0.20 |
| from 101 to 150 | 0.13 |
| from 151 to 200 | 0.10 |

The substance to be analyzed must be weighed with an approximation of 0.1 mg in a glass weight-thimble (6.1).

8.2 Procedure

Pour the substance to be analyzed into an Erlenmeyer flask of 500 ml (6.2). Add 20 ml of solvent (5.4) in order to dissolve the fatty matter. Add exactly 25 ml of the Wijs reagent (5.5), insert the stopper, shake the contents and leave the Erlenmeyer flask in the dark. Do not use a mouth pipette for the Wijs reagent. Prepare a blank, in the same way, with the solvent and reagent, without the substance to be analyzed. Keep the Erlenmeyer flask in the dark for 1 hour, if the substance has an iodine number lower than 150; for substances having an iodine number higher than 150 and for polymerized products or highly oxidized products, keep the Erlenmeyer flasks in the dark for 2 hours. Then add 20 ml of the potassium iodide solution (5.1) and 150 ml of water to each Erlenmeyer flask. Titrate with the standard volumetric solution of sodium thiosulfate (5.3) until the yellow colouring due to the iodine has almost disappeared. Add a few drops of the starch solution (5.2) and continue the titration until the blue colouring has just disappeared after vigorous shaking.

Note—The potentiometric determination of the final point is allowed.

8.3 Number of Tests

Two tests should be carried out on the same sample.

9. Results

The iodine number is obtained through the following expression:

$$12.69\ c(V_1-V_2)/m$$

wherein:

$c$=is the exact concentration (moles/liter) of the titrated sodium thiosulfate solution (5.3) used;

$V_1$=is the value of the volume (ml) of the titrated sodium thiosulfate solution (5.3) used;

$V_2$=is the value of the volume (ml) of the sodium thiosulfate solutions (5.3) used for the determination;

m=is the weight (g) of the substance to be analyzed (7).

The result will be the arithmetical average of two tests.

EXAMPLE 7

Description of a completely vegetable oil obtained exclusively from the mesocarp of the fruit of some varieties of *Elaeis Guineensis* (oil palm) and subsequently refined for use according to the present invention.

| | Method | Unit | Standard Values |
| --- | --- | --- | --- |
| Physico-chemical Characteristics | | | |
| Humidity | NGD C 3-1976 | % | 0.10 max. |
| F.F.A.(oleic acid) | NGD C10-1976 | % | 0.15 max. |
| Number of peroxides | NGD C35-1976 | $MeqD_2$/Kg | 2.0 max. |
| Rancidity | NGD C56-1976 | | negative |
| Iodine number | NGD C32-1972 | $GI_2/100$ g | 48-53 |
| Flow point (open capillary) | NGD C27-1976 | °C. | 37-39 |
| Smoke point | NGD C77-1989 | °C. | 215 min. |
| Oxidation Stability | Rancimat (120° C.) | hrs | 11 min. |
| GLC Analysis | NGD C41, 42-1976 | % | |
| C12 lauric acid | | | 1.0 max. |
| C14 myristic acid | | | 1.5 max. |
| C16 palmitic acid | | | 42-47 |
| C18 stearic acid | | | 3-5 |
| C18:1 oleic acid | | | 27-42 |
| C18:2 linoleic acid | | | 8-12 |
| C18:3 linoleic acid | | | 0.5 max. |
| S.F.I. (NMR) | NGD Db10-1975 | % | |
| 10° C. | | | 48-56 |
| 20° C. | | | 23-28 |
| 30° C. | | | 7-12 |
| 35° C. | | | 4-7 |
| Average nutritional information for 100 g of product | | | |
| Energetic value | | Kcal | 900 |
| | | Kjoule | 3700 |
| Fatty matter | | g | 100.0 |
| Microbiological characteristics | | | |
| total bacterial charge | | U.F.C./g | <10 |
| mildew and yeasts | | U.F.C./g | <10 |
| pathogens | | | absent |
| Packaging: | | | |

The product is delivered in the solid state, in polyethylene bags for food, contained in cardboard boxes sealed with adhesive tape. Net weight 25 kg.

Conservation: preferably at max. 18° C.

Shelf-life: 8 (eight) months.

EXAMPLE 8

Method for the Preparation of a Rat-Poisoning Composition According to the Invention Equipment Used for Preparing the Formulate:

Calibrated precision balances.

Storage silos for flour.

Pneumatic pump.

Dosage machine.

Procedure.

The operator should have personal protection systems such as polyethylene gloves, overall, powder mask, and activates all passive and active safety devices.

The inert raw materials forming the formulate are weighed.

The active principles, dyes, preservatives and the fragrance contained in the formulate are weighed and transferred to the mixer together with the superfine "00" flour coming from the silos situated outside the facility, by means of a pneumatic pump. All the other raw materials, previously weighed, are charged into the mixer:

Superfine "00" flour

Ground biscuit

Preservatives

Triethanol amine

Refined palm oil

Saccharine

Refined sugar free or micro-encapsulated anticoagulant active principle.

Denatonium Benzoate

After filling the mixer, the mixing operation is started. The mixing is carried out until a paste is obtained having a homogeneous colouring and consistency, with no lumps.

The paste, when ready, is subjected to quality control and, if homogeneous, is sent for packaging by means of measuring devices.

The invention claimed is:

1. A rodenticidal composition in the form of vegetable paste, which consists of:

| | |
|---|---|
| superfine "00" flour | 49.1565% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| brodifacoum | 0.005% |
| denatonium benzoate | 0.001%. |

2. A rodenticidal composition which consists of:

| | |
|---|---|
| superfine "00" flour | 49.1565% |
| ground biscuit | 12.500% |
| preservatives | 2.000% |
| triethanol amine | 0.075% |
| refined palm oil | 25.000% |
| saccharine | 0.0125% |
| refined sugar | 11.250% |
| brodifacoum | 0.005% |
| denatonium benzoate | 0.001%. |

* * * * *